US012348925B2

United States Patent
LeBoeuf et al.

(10) Patent No.: US 12,348,925 B2
(45) Date of Patent: *Jul. 1, 2025

(54) RINGED-SHAPED BIOMETRIC EARPIECE

(71) Applicant: YUKKA MAGIC LLC, Wilmington, DE (US)

(72) Inventors: Steven Francis LeBoeuf, Raleigh, NC (US); Shawn M. Stephenson, Raleigh, NC (US); Macintosh E. Perry, Garner, NC (US)

(73) Assignee: YUKKA MAGIC LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/622,382

(22) Filed: Mar. 29, 2024

(65) Prior Publication Data

US 2024/0267664 A1 Aug. 8, 2024

Related U.S. Application Data

(63) Continuation of application No. 17/427,459, filed as application No. PCT/US2020/017856 on Feb. 12, 2020, now Pat. No. 11,950,039.

(60) Provisional application No. 62/805,183, filed on Feb. 13, 2019.

(51) Int. Cl.
*H04R 1/10* (2006.01)
*A61B 5/00* (2006.01)
*A61B 5/11* (2006.01)
*H04B 10/11* (2013.01)

(52) U.S. Cl.
CPC ......... *H04R 1/1016* (2013.01); *A61B 5/0002* (2013.01); *A61B 5/1126* (2013.01); *A61B 5/6817* (2013.01); *H04B 10/11* (2013.01); *H04R 1/1025* (2013.01); *A61B 2560/0219* (2013.01); *A61B 2562/164* (2013.01);
(Continued)

(58) Field of Classification Search
CPC ................ H04R 1/1016; H04R 1/1025; H04R 2420/07; H04R 2460/09; A61B 5/0002; A61B 5/1126; A61B 5/6817; A61B 2560/0219; A61B 2562/164; A61B 2562/223; H04B 10/11
See application file for complete search history.

(56) References Cited

U.S. PATENT DOCUMENTS

| 8,788,002 B2 | 7/2014 | Leboeuf et al. |
| 9,660,488 B2 | 5/2017 | Breedvelt |
| 9,716,779 B1 * | 7/2017 | Nicodemus ............. G06F 1/163 |

(Continued)

FOREIGN PATENT DOCUMENTS

JP 2012257049 12/2012

*Primary Examiner* — Jason R Kurr
(74) *Attorney, Agent, or Firm* — Brownstein Hyatt Farber Schreck, LLP

(57) ABSTRACT

A wearable device includes a ring-shaped housing having a central opening and defining an annular interior volume. The housing is configured to be worn within an ear of a subject such that the subject's ear canal is exposed by the central opening. At least one optical emitter and at least one optical detector are supported within the housing. The housing includes at least one window through which light can be delivered from the at least one optical emitter to the ear, and through which light from the ear can be delivered to the at least one optical detector.

19 Claims, 17 Drawing Sheets

(52) U.S. Cl.
CPC .... *A61B 2562/223* (2013.01); *H04R 2420/07* (2013.01); *H04R 2460/09* (2013.01)

(56) References Cited

U.S. PATENT DOCUMENTS

| | | | |
|---|---|---|---|
| 2006/0218969 A1* | 10/2006 | Cleofas | A44C 9/0023 63/15.4 |
| 2015/0366475 A1 | 12/2015 | Just et al. | |
| 2016/0344436 A1 | 11/2016 | Oh | |
| 2017/0119315 A1 | 5/2017 | Leboeuf et al. | |
| 2018/0302709 A1* | 10/2018 | Wagner | A61B 5/0261 |
| 2019/0014403 A1 | 1/2019 | Lee | |
| 2019/0320256 A1 | 10/2019 | Igarashi | |
| 2019/0381672 A1 | 12/2019 | Hosoi | |
| 2022/0312101 A1 | 9/2022 | Nakagawa | |
| 2022/0394370 A1 | 12/2022 | Sarbou | |

* cited by examiner

RINGED-SHAPED BIOMETRIC EARPIECE

CROSS-REFERENCE TO RELATED APPLICATION(S)

This application is a continuation patent application of U.S. patent application Ser. No. 17/427,459, filed Jul. 30, 2021, and titled "Ringed-Shaped Biometric Earpiece", which is a National Stage of International Application No. PCT/US20/17856, filed Feb. 12, 2020, and titled "Ringed-Shaped Biometric Earpiece", and claims the benefit of U.S. Provisional Patent Application No. 62/805,183 filed Feb. 13, 2019, titled "Ringed-Shaped Biometric Earpiece", the disclosures of which are incorporated herein by reference as if set forth in its entirety.

FIELD

The present invention relates generally to wearable devices, and more particularly to ear worn devices.

BACKGROUND

Smart audio earpieces with sensors, often referred to as "hearable" devices are increasingly being adopted by consumers. Largely due to their advanced features, such as multimedia functionality and smart audio features, hearable devices are often being worn for longer periods of time than traditional audio headphones. However, conventional hearable devices may be relatively bulky and uncomfortable, and in some cases painful, to wear for long periods of time. Additionally, conventional hearable devices may be inconvenient to keep on one's person when not in use. As such, often times these hearable devices are not available for use when most desired.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a wearable device includes a ring-shaped housing having a central opening and defining an annular interior volume. The housing is configured to be worn within an ear of a subject such that the subject's ear canal is exposed by the central opening. In some embodiments, the housing is formed from a conformable, resilient material that facilitates retention of the device in a user's ear in a comfortable manner. In some embodiments, the housing may include a stabilizer fin or member extending outwardly therefrom that is configured to engage a portion of the ear and help secure the housing within the ear in a comfortable manner. In addition, in some embodiments, one or more electrical components, such as sensors, processors, and the like, can be housed within the stabilizer member.

In some embodiments, the housing includes an outer annular cover and an inner annular cover that are secured together. The outer and inner covers may be removably secured together so as to facilitate replacement of the outer cover, thereby allowing for adjusting the size and/or shape of an outer cover that best fits a user's ear. The outer cover is formed from a conformable, resilient material. In addition, the outer cover may include a portion configured to matingly engage with a portion of the inner cover to prevent relative rotation of the outer and inner covers, and referred to as a "clocking" feature.

At least one optical emitter and at least one optical detector are supported within the housing. The housing includes at least one window through which light can be delivered from the at least one optical emitter to the ear, and through which light from the ear can be delivered to the at least one optical detector. In some embodiments, the at least one window is at least one transparent portion in the housing. In other embodiments, the at least one window is at least one opening in the housing. In other embodiments, the at least one window includes first and second windows, wherein the first window is configured to deliver light from the at least one optical emitter to the ear, and wherein the second window is configured to deliver light from the ear to the at least one optical detector.

In some embodiments, the wearable device includes at least one speaker within the housing. The housing may include one or more apertures through which sound from the at least one speaker can pass. In some embodiments, the at least one speaker may have an arcuate configuration to better fit within the annular interior volume of the housing. In other embodiments, a speaker may be positioned within the central opening of the housing via at least one support member extending radially inwardly from the housing.

The wearable device may also include various other electronic components. For example, the wearable device may include at least one processor, at least one power source, a wireless communication unit, a microphone, and at least one motion sensor that is configured to sense body motion of the subject wearing the device. The at least one processor is in communication with the various electronic components within the device and may be configured to control operation thereof. For example, the at least one processor may be configured to control the at least one optical emitter to emit light, and to process signals containing physiological information produced by the at least one optical detector. In addition, the at least one processor may be configured to control wireless communications via the wireless communication unit. The various electronic components may be supported by a flexible printed circuit, hereinafter referred to as a "flex circuit", that can be shaped to conform within the annular interior volume of the housing.

In some embodiments, the at least one optical emitter and the at least one optical detector include a first optical emitter, a first optical detector, a second optical emitter, and a second optical detector. The first optical detector and the first optical emitter are in adjacent relationship at a first location within the housing with a first optical crosstalk barrier therebetween, and the second optical detector and the second optical emitter are in adjacent relationship at a second location within the housing with a second optical crosstalk barrier therebetween. In some embodiments, the first optical detector and the first optical emitter may be optically isolated from the second optical detector and the second optical emitter via at least one optical barrier.

In some embodiments, light guiding material is provided within the housing that is in optical communication with the at least one optical emitter and the at least one window and that is configured to guide light from the at least one optical emitter to the at least one window. In addition, or alternatively, light guiding material may be provided within the housing that is in optical communication with the at least one optical detector and the at least one window and that is configured to guide light from the at least one window to the at least one optical detector.

In some embodiments, a power source for the wearable device may include at least one rechargeable battery, and at least one charging coil may be provided within the housing or as part of the housing to transfer electrical charge to the at least one rechargeable battery when the housing is within a pre-determined range of an inductive charging coil.

In some embodiments, the wearable device may include at least one magnet that is configured to magnetically secure the housing to another device, such as a mobile phone, in order to provide convenient storage and access. The at least one magnet may be within the housing, a part of the housing, or located external to the housing.

Embodiments of the present invention provide very lightweight hearable devices that can be worn for extremely long periods of time without noteworthy discomfort and without significantly attenuating outside external sounds. In addition, such devices can be easily stored within or on portable mobile devices such that they are readily available when needed.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

DETAILED DESCRIPTION

Figure 1:
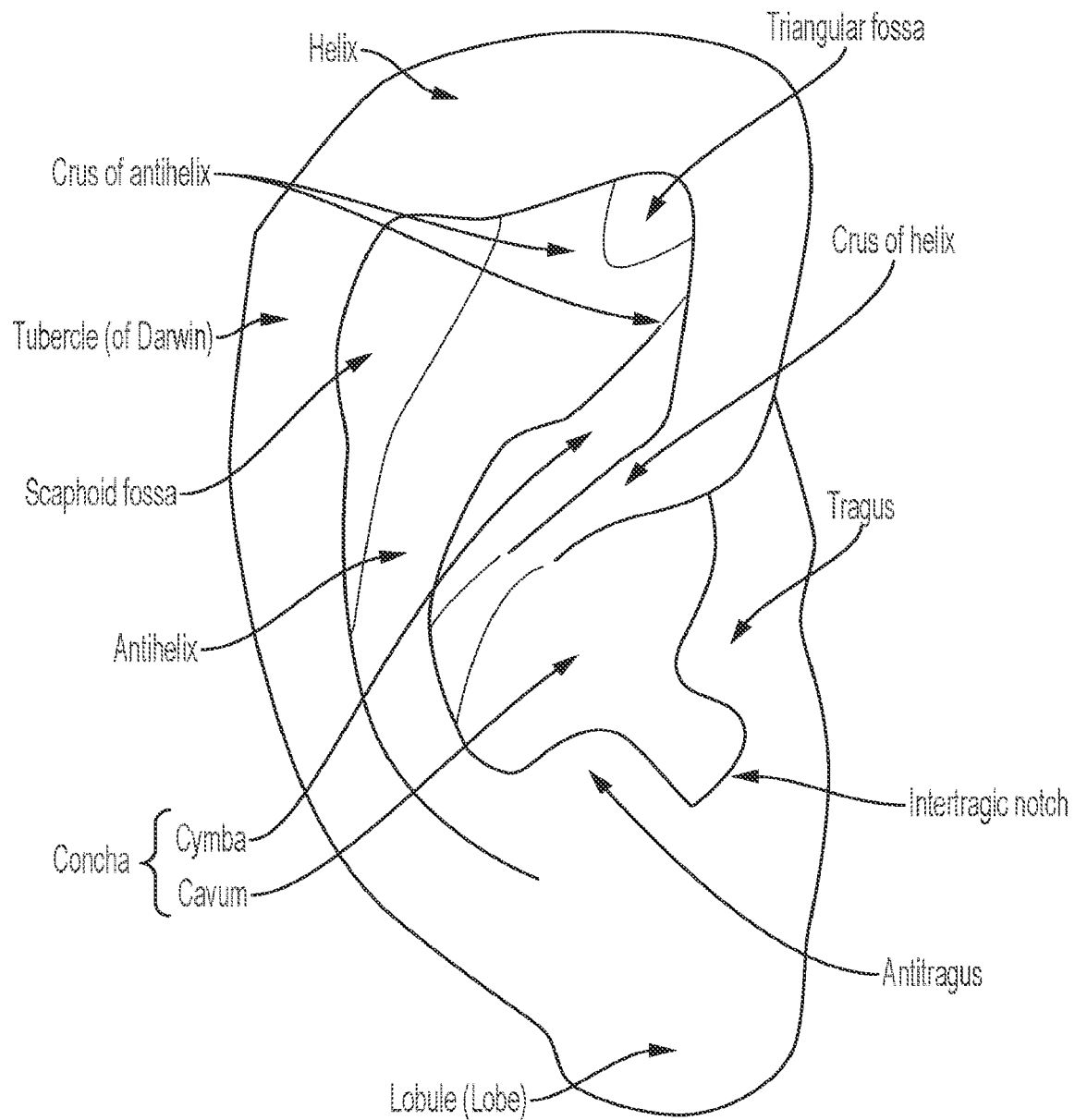
FIG. 1 illustrates the anatomy of a human ear.

The present invention will now be described more fully hereinafter with reference to the accompanying figures, in which embodiments of the invention are shown. This invention may however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled", or "secured" to another feature or element, it can be directly connected, attached, coupled, or secured to the other feature or element or intervening features or elements may be present. In contrast, when a feature or element is referred to as being "directly connected", "directly attached", "directly coupled", or "directly secured" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary, for example, by as much as +/−20%.

The terms "optical source" and "optical emitter", as used herein, are interchangeable.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" may include monitoring blood gas levels, blood hydration, and metabolite/electrolyte levels, etc.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) that may wear a device according to embodiments of the present invention.

The term "coupling", as used herein, refers to the interaction or communication between excitation energy entering a region of a body and the region itself. For example, one form of optical coupling may be the interaction between excitation light generated from an optical emitter and the blood vessels of the body of a user. In one embodiment, this interaction may involve excitation light entering the ear region and scattering from a blood vessel in the ear such that the intensity of scattered light is proportional to blood flow within the blood vessel.

The term "processor" is used broadly to refer to a signal processor or computing system or processing or computing method which may be localized or distributed. For example, a localized signal processor may comprise one or more signal processors or processing methods localized to a general location, such as to an earbud. Examples of a distributed processor include "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. Microprocessors, microcontrollers, ASICs (application specific integrated circuits), analog processing circuitry, made-for AI (artificial intelligence or neural network) circuitry, and digital signal processors are a few non-limiting examples of physical signal processors that may be found in wearable devices.

The term "remote" does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. However, any wireless device (such as a portable device, for example) or system (such as a remote database for example) is considered remote to any other wireless device or system.

Figure 2B:
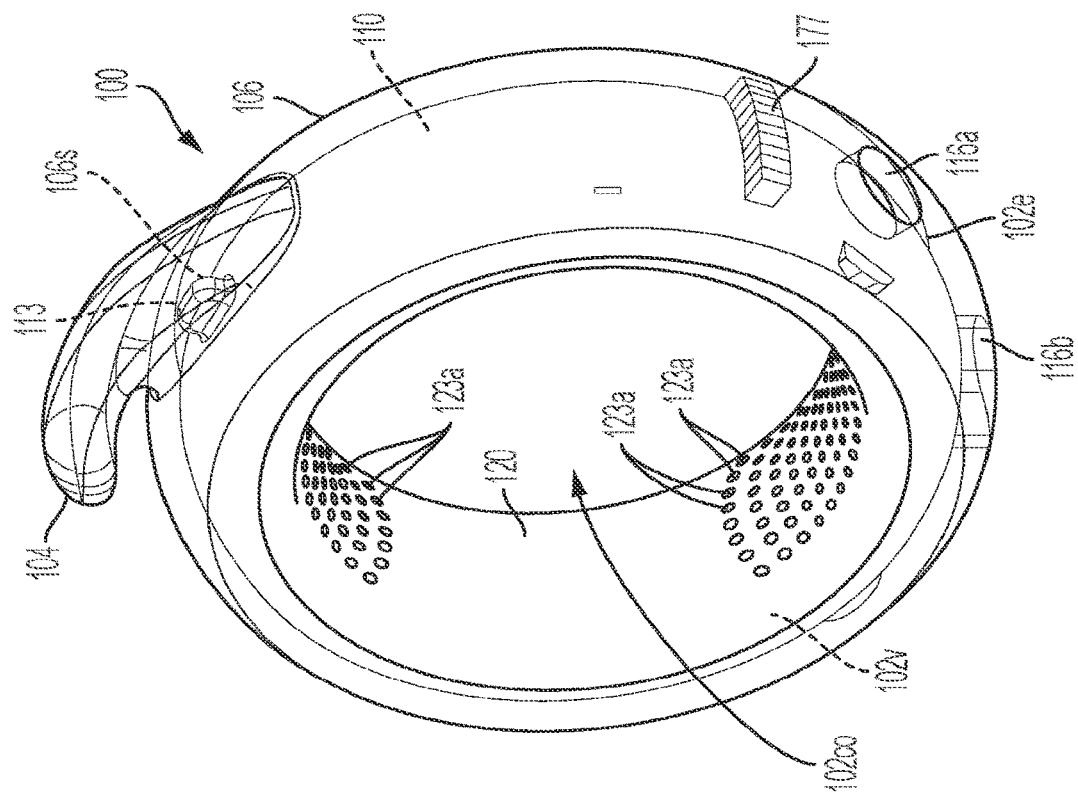
FIG. 2B is an opposite perspective view of the wearable device of FIG. 2A.
Figure 2A:
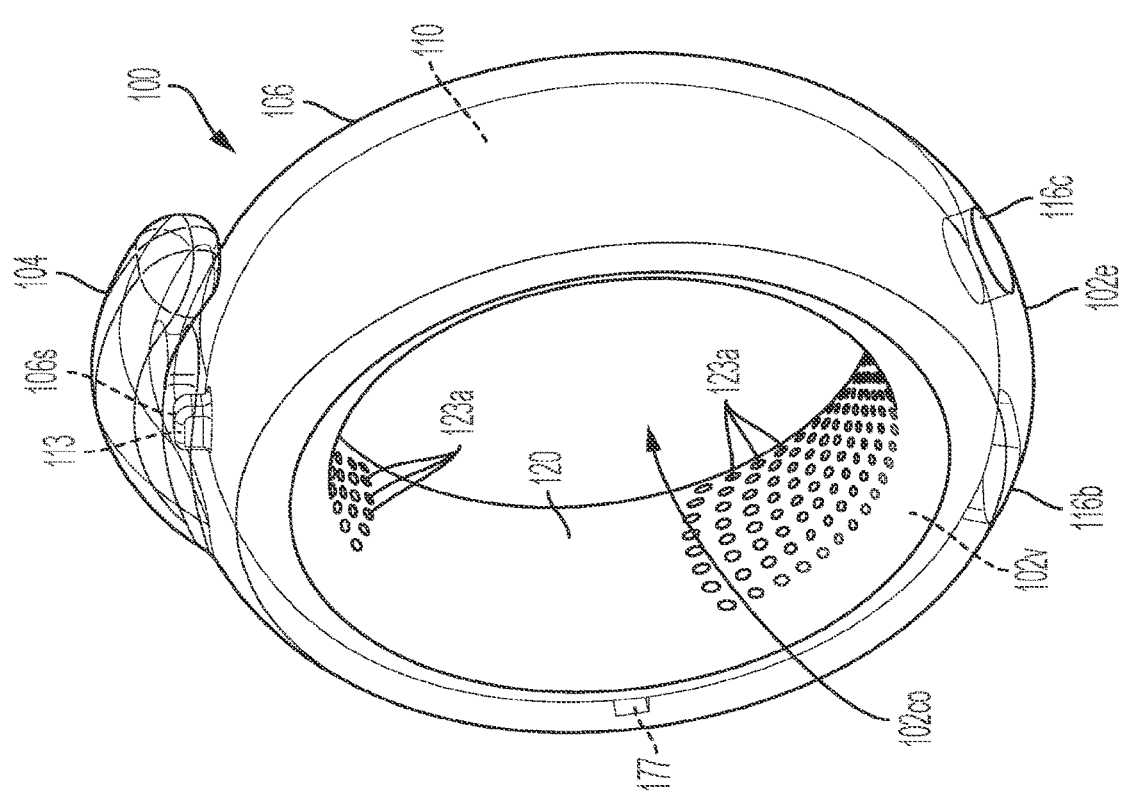
FIG. 2A is a perspective view of a wearable device according to some embodiments of the present invention.

Referring now to the drawings, some embodiments of the present invention are illustrated. FIGS. 2A-2B illustrate a wearable device 100 configured to be worn comfortably in the ear of a user for extended periods of time. The wearable device 100 includes a "loop" or "ring-shaped" housing 102 having a central opening 102co and defining an annular interior volume 102v. An outer covering 106 of soft, conformable material, such as silicone or other soft, thermoplastic elastomers, is removably secured to the housing 102. This outer covering 106 may be removably secured to the housing 102 so as to facilitate replacement of the outer covering 106, thereby allowing a user to adjust the size and/or shape of the outer covering 106 that best fits the user's ear.

Figure 8A:
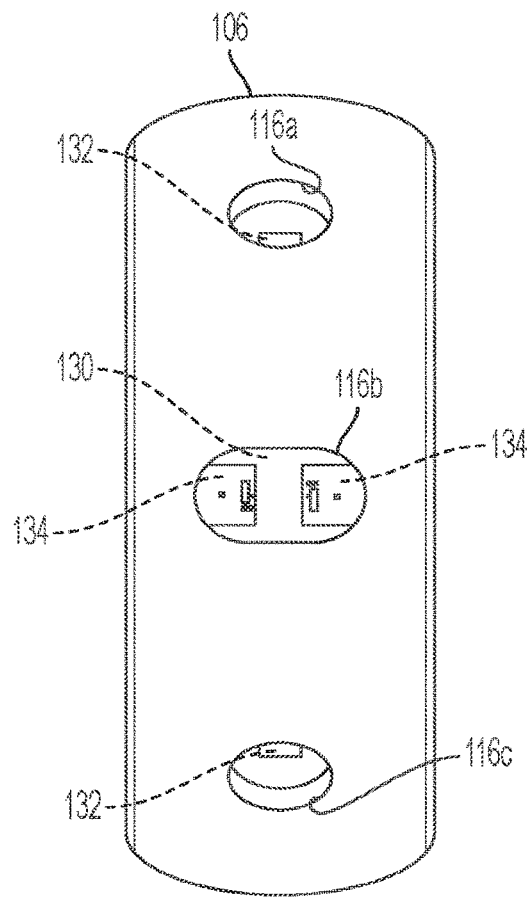
FIG. 8A is a side view of a wearable device according to some embodiments of the present invention with an opaque outer cover.
Figure 8B:
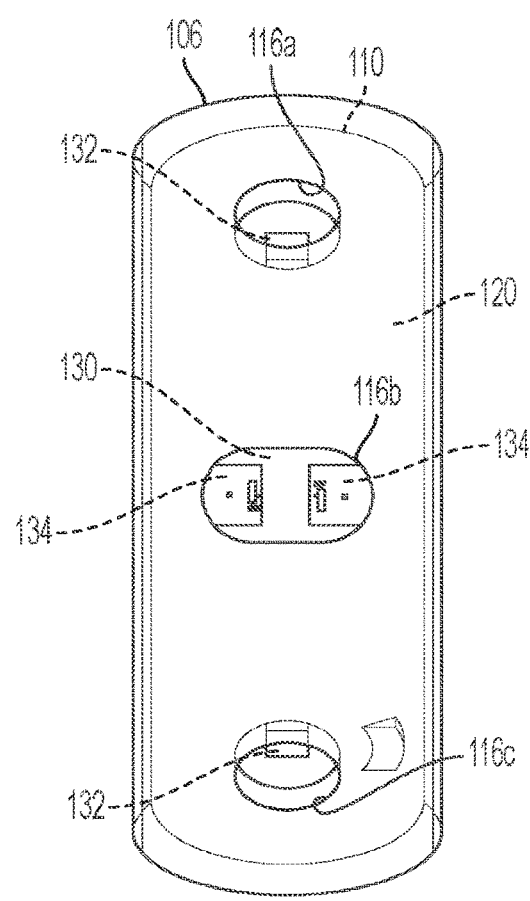
FIG. 8B is a side view of a wearable device according to some embodiments of the present invention with a transparent outer cover.
Figure 9A:
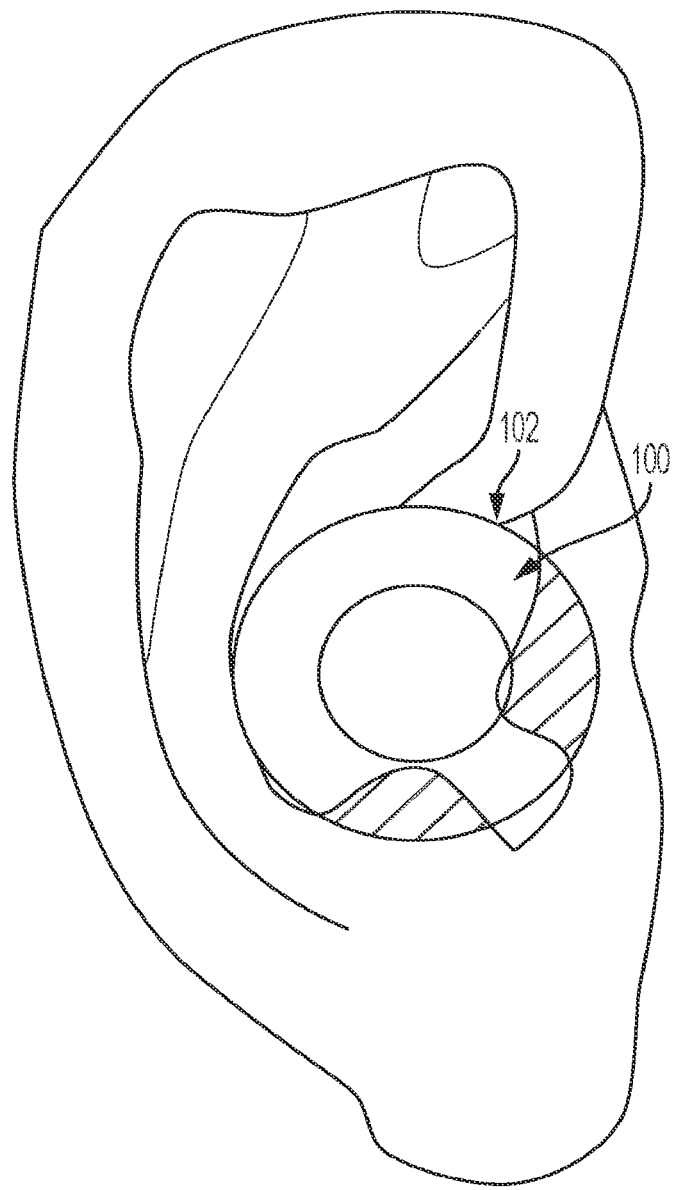
FIG. 9A is a schematic illustration of a ring-shaped wearable device, such as the device of FIG. 7, positioned within an ear.
Figure 9B:
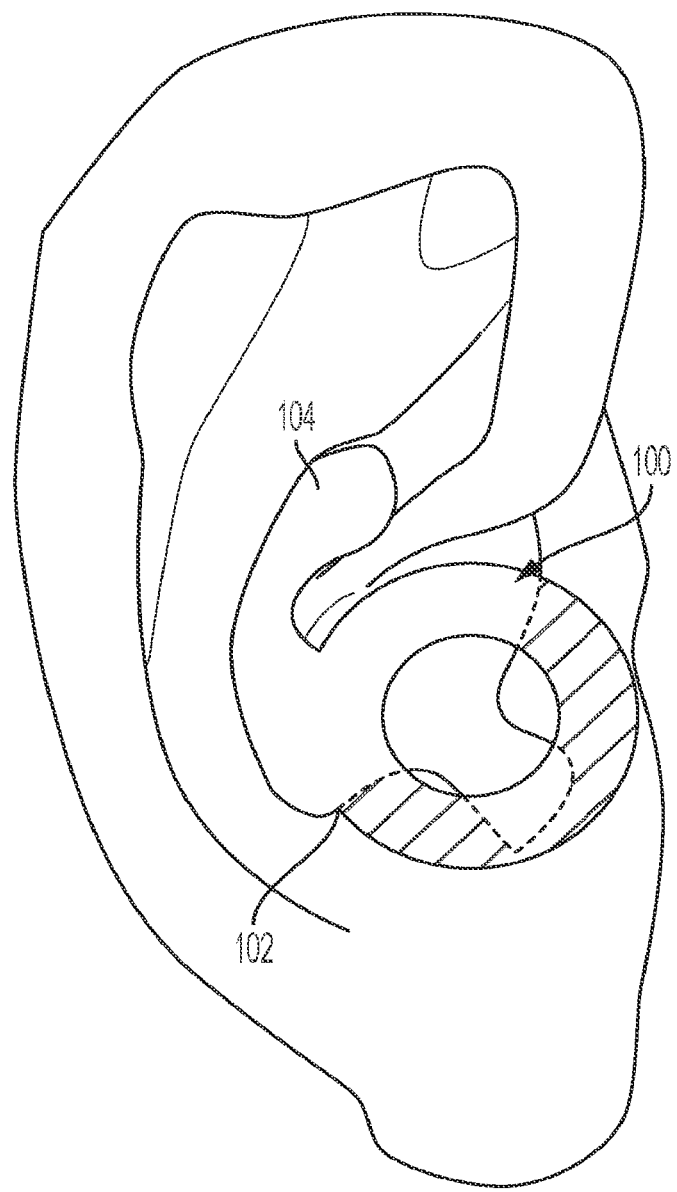
FIG. 9B is a schematic illustration of a ring-shaped wearable device having a stabilizer member, such as the device of FIGS. 2A-2B, wherein the device is positioned within an ear and at least partially supported by the crux of the helix and by the support member contacting the antihelix.
Figure 10A:
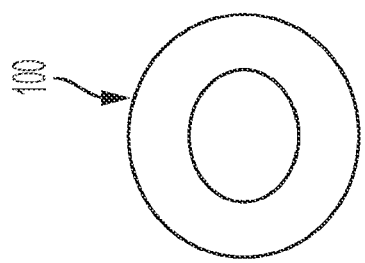
FIGS. 10A-10E are schematic illustrations of various, non-limiting shapes that "ringed-shaped" wearable devices according to embodiments of the present invention can have.
Figure 10B:
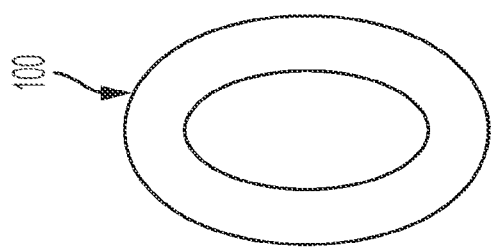
Figure 10C:
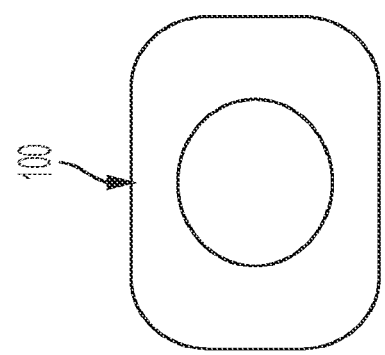
Figure 10D:
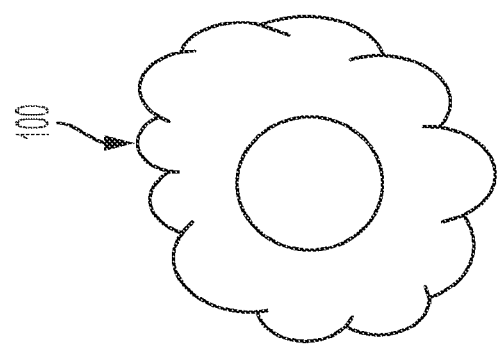
Figure 10E:
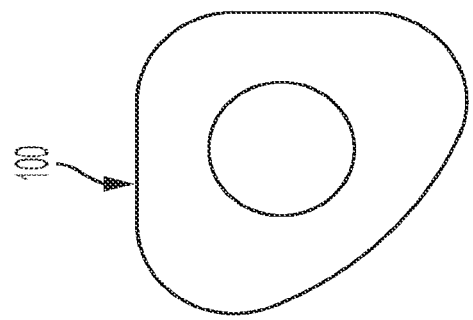

The illustrated outer covering 106 includes a stabilizer fin or member 104 extending outwardly therefrom that is configured to engage a portion of the ear, such as the antihelix, as illustrated schematically in FIG. 9B. The stabilizer member 104 helps secure the housing 102 within the ear in a comfortable manner. However, the outer covering 106 is not required to have such a stabilizer member. In the illustrated embodiment, the housing 102 includes a protrusion 113 that is configured to matingly engage with a corresponding slot or cavity 106s in the outer covering 106 to prevent relative rotation (also referred to as "clocking") of the housing 102 and the outer covering 106. In some embodiments, the material of the outer covering 106 may be opaque (FIG. 8A), and in other embodiments, the material of the outer covering 106 may be transparent or partially transparent (FIG. 8B).

Figure 3:
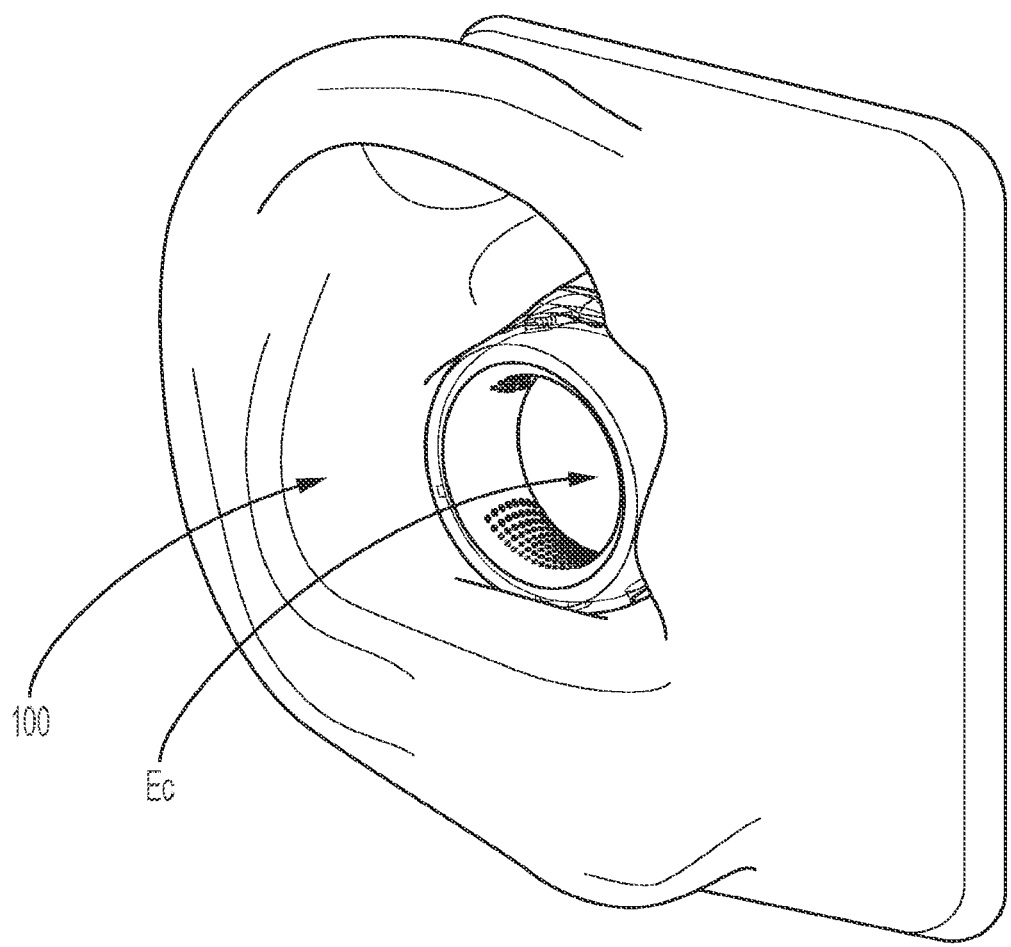
FIG. 3 illustrates the wearable device of FIGS. 2A-2B positioned within the ear of a person.

The ring-shaped device 100 is configured to be worn within an ear of a subject such that the subject's ear canal EC is exposed by the central opening 102co of the housing 102, as illustrated in FIG. 3. In other words, the device 100 does not obstruct access to the ear canal EC or hinder sound from entering the ear canal EC. The shape of the device 100 is such that the device 100 is placed in the conchae of the ear with a portion thereof held comfortably in place, at least partially, by the tragus and antitragus, as illustrated schematically in FIG. 9A. In addition, another portion of the device 100 may engage the antihelix of the ear, as illustrated in FIG. 9A, which further helps comfortably secure the device 100 within the ear. The ring-shaped device 100 may have various configurations and need not be circular in configuration. For example, the term "ring-shaped" is intended to include any shape that allows the device 100 to be worn within an ear while also having a central opening 102co that exposes the ear canal EC and does not hinder sound passing through the opening 102co into the ear canal EC. FIGS. 10A-10E illustrate various non-limiting structures that are ring-shaped in accordance with embodiments of the present invention.

The illustrated device 100 has a substantially circular configuration. However, embodiments of the present invention are not limited to the illustrated shape of the device 100. The device 100 may have various shapes and configurations. For example, FIGS. 10A-10E schematically illustrate various non-limiting shapes that the device 100 can have. Other shapes not illustrated are possible, also. For example, each of the illustrated devices 100 in FIGS. 10A-10E could have one or more stabilizer members, such as the stabilizer member 104 illustrated in FIGS. 2A-2B.

Figure 4B:
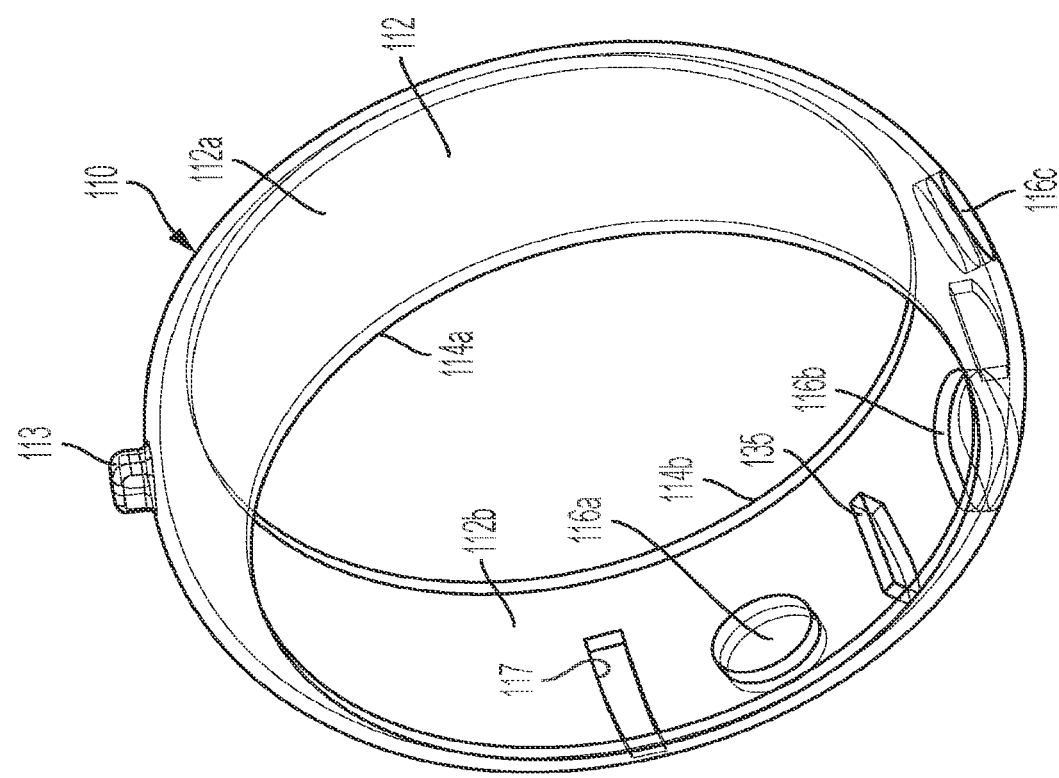
FIGS. 4A and 4B illustrate respective inner and outer annular covers of a wearable device, according to some embodiments of the present invention.
Figure 4A:
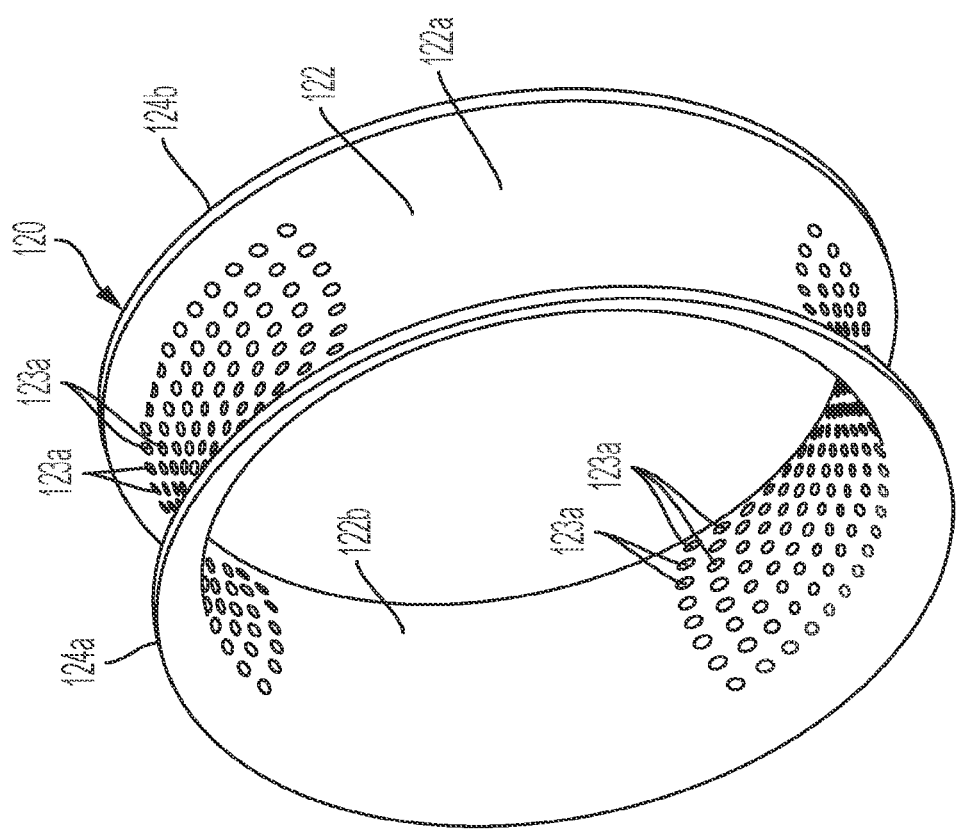
Figure 5A:
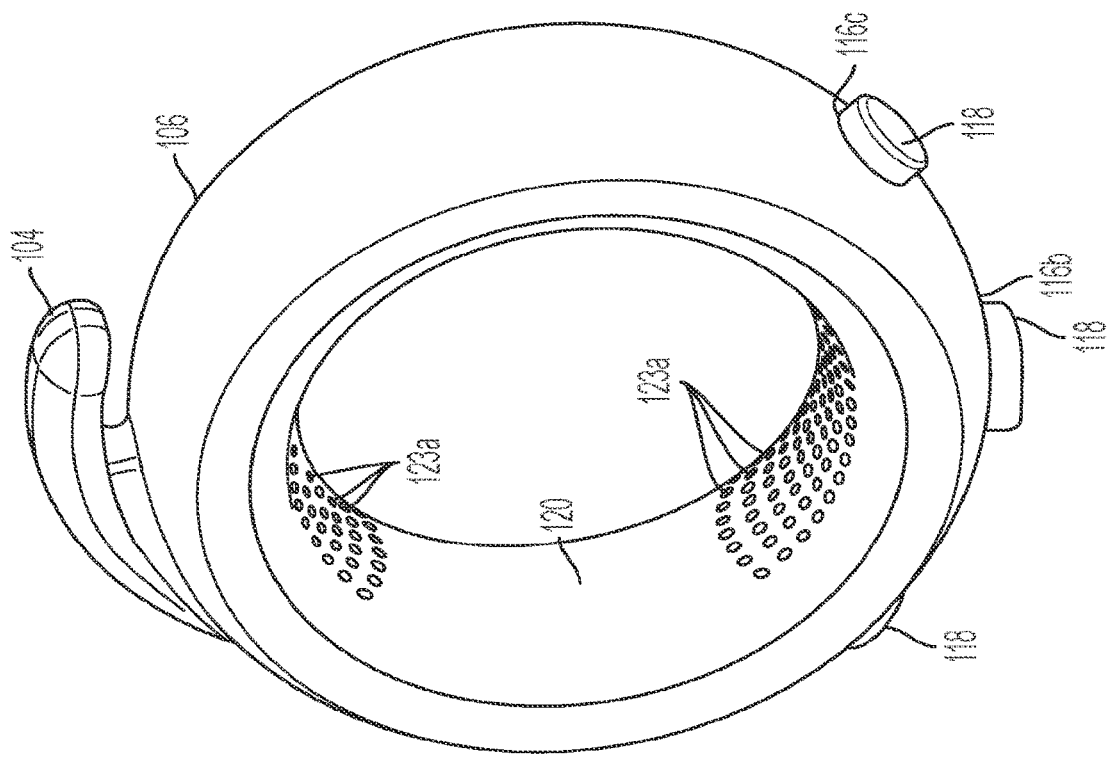
FIG. 5A illustrates the inner and outer covers of FIGS. 4A and 4B assembled together to form a housing.

Referring to FIGS. 4A-4B, a housing 102 for a wearable device 100, according to some embodiments of the present invention, includes an outer cover 110 (FIG. 4B) and an inner cover 120 (FIG. 4A). The inner cover 120 has an annular wall 122 with opposite outer and inner surfaces 122a, 122b, and opposed first and second annular edges 124a, 124b. The annular wall 122 has a concave configuration facing outwardly, as illustrated (i.e., the outer surface 122a is concave and the inner surface 122b is convex). The outer cover 110 has an annular wall 112 with opposite outer and inner surfaces 112a, 112b, and opposed first and second annular edges 114a, 114b. The annular wall 112 has a concave configuration facing inwardly, as illustrated (i.e., the outer surface 112a is convex and the inner surface 112b is concave). The outer and inner covers 110, 120 are configured to be removably secured to each other such that the concave inner surfaces 112b, 122b face each other and form the annular interior volume 102v (FIG. 5A). The respective annular edges 114a, 114b, 124a, 124b of the outer and inner covers 110, 120 are configured to form a seal to prevent the ingress of moisture and debris into the annular interior volume 102v. In some embodiments, the outer cover 110 may include a portion (not shown) configured to matingly engage with a portion (not shown) of the inner cover 120 to prevent rotation of the outer cover 110 relative to the inner cover 120. Such features are referred to as "clocking" features.

In some embodiments, the outer and inner covers 110, 120 may be removably secured together so as to facilitate replacement of the outer cover 110, thereby allowing a user to adjust the size and/or shape of the outer cover 110 that best fits the user's ear. The electronics within the housing 102 may be protected by a shield or other structure that prevents damage to the electronics, when removing and/or replacing the outer cover 110.

The outer and inner covers 110, 120 may be formed from conformable, resilient materials, such as silicone or other soft, thermoplastic elastomers. In some embodiments, the inner cover 120 may be formed from a rigid or substantially rigid material, and the outer cover 110 is formed from a conformable, resilient material. In embodiments where the inner cover 120 is formed from a rigid or substantially rigid material, exemplary such materials may include, but are not limited to, ceramics, glass, composites such as carbon fiber, metals or metal alloys, alone or in combination.

As illustrated in FIG. 4A, the inner cover 120 includes two sets of apertures 123a that allow sound from respective speakers 140 (described below) within the housing 102 to pass therethrough. As illustrated in FIG. 4B, the outer cover 110 includes multiple windows 116a, 116b, 116c that allow light to pass therethrough, as will be described below. In some embodiments, one or more of the windows 116a, 116b, 116c may be transparent portions in the outer cover 110 (and in the outer covering 106 when utilized). In other embodiments, one or more of the windows 116a, 116b, 116c may be an opening in the outer cover 110 (and in the outer covering 106 when utilized) with or without transparent material within the opening. In the illustrated embodiment, the outer cover 110 (and in the outer covering 106 when utilized) also includes an opening 117 through which one or more electrodes 177 may extend for contacting the skin of a wearer of the device 100.

Additionally, the outer covering 106, when utilized, may include regions of conductive and nonconductive silicone, and the conductive regions may serve as electrodes which are in electrical communication with the electrodes 177. A key benefit of such a configuration is that the silicone may at least partially conform to the person's ear and hence better electrically couple to the person's skin, reducing contact resistance and reducing the electrical resistance variation from motion artifacts. Multiple electrode regions across the outer covering 106 may be used to assess ECG (electrocardiogram), EEG (electroencephalogram), EOG (electrooculography), EMG (electromyography), galvanic skin response, and the like.

In some embodiments, a wearable device 100 does not utilize an outer covering 106 surrounding the housing 102. Instead, the housing 102 is configured to be attached within an ear of a user and the outer cover 110 serves the function of the outer covering 106 described above.

Figure 6B:
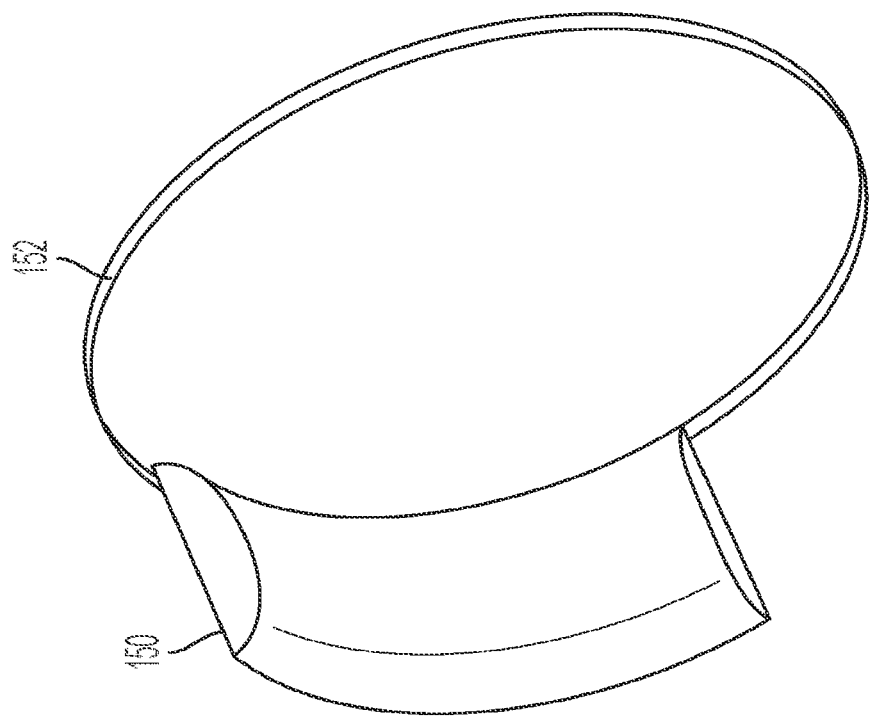
FIG. 6B illustrates the battery and inductive charging coil(s) of FIG. 6A separated from the flex circuit and the other electronic components for clarity.
Figure 6A:
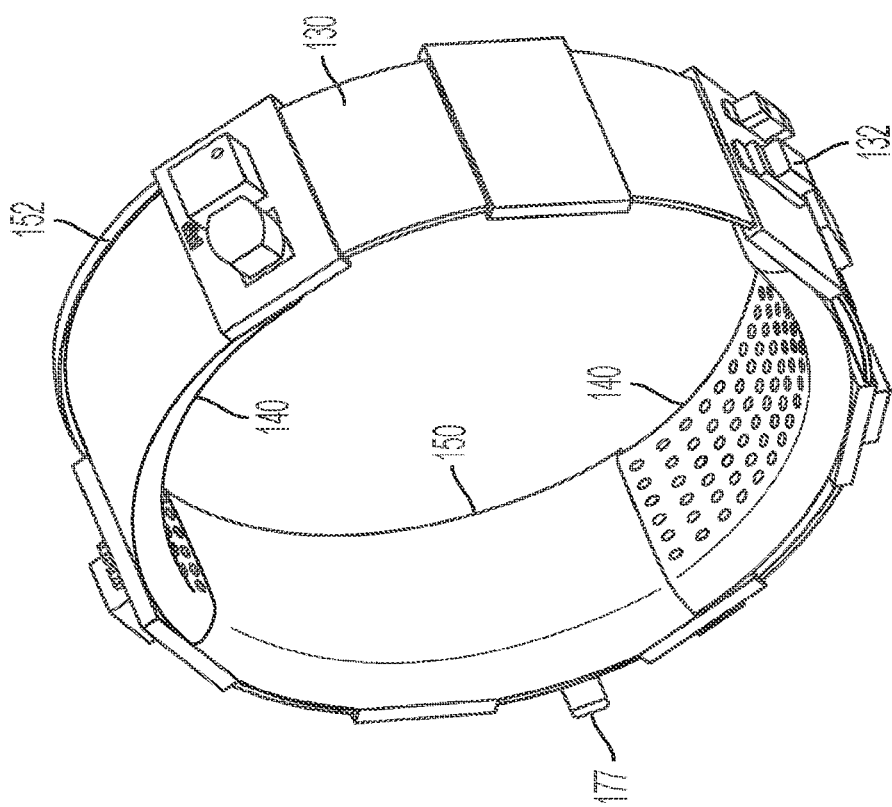
FIG. 6A is a perspective view of a flex circuit that can be located within a wearable device according to some embodiments of the present invention, and that supports various electronic components such as optical emitters and detectors, speakers, a battery, and inductive charging coil(s).
Figure 6D:
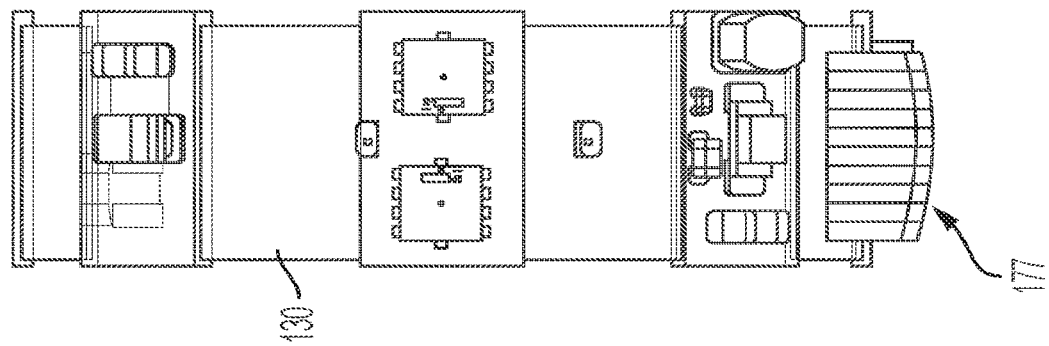
FIG. 6D illustrates various electrical components supported by the flex circuit of FIG. 6A.
Figure 6C:
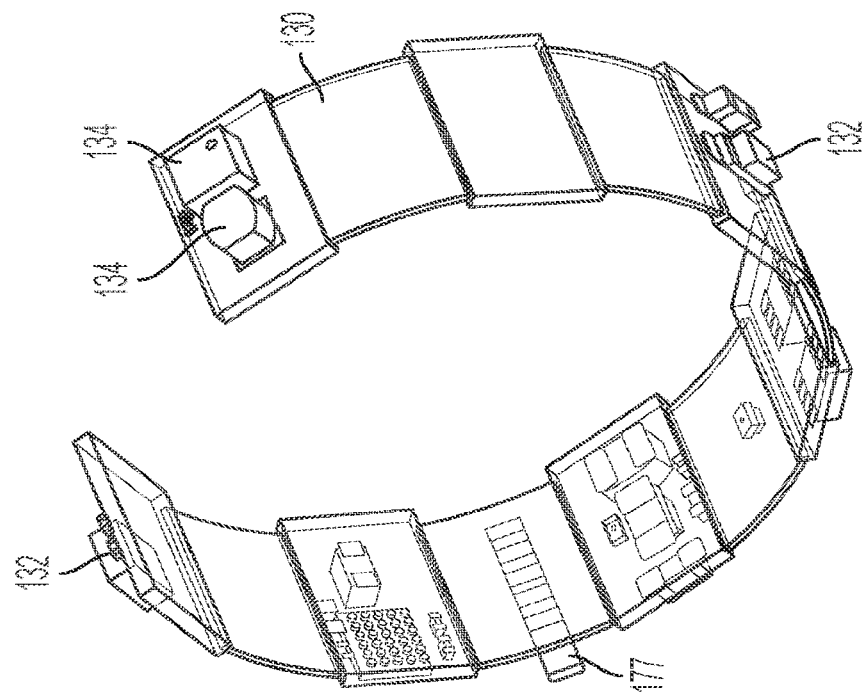
FIG. 6C is a perspective view of the flex circuit of FIG. 6A with the battery, speakers and inductive charging coil removed for clarity.
Figure 7:
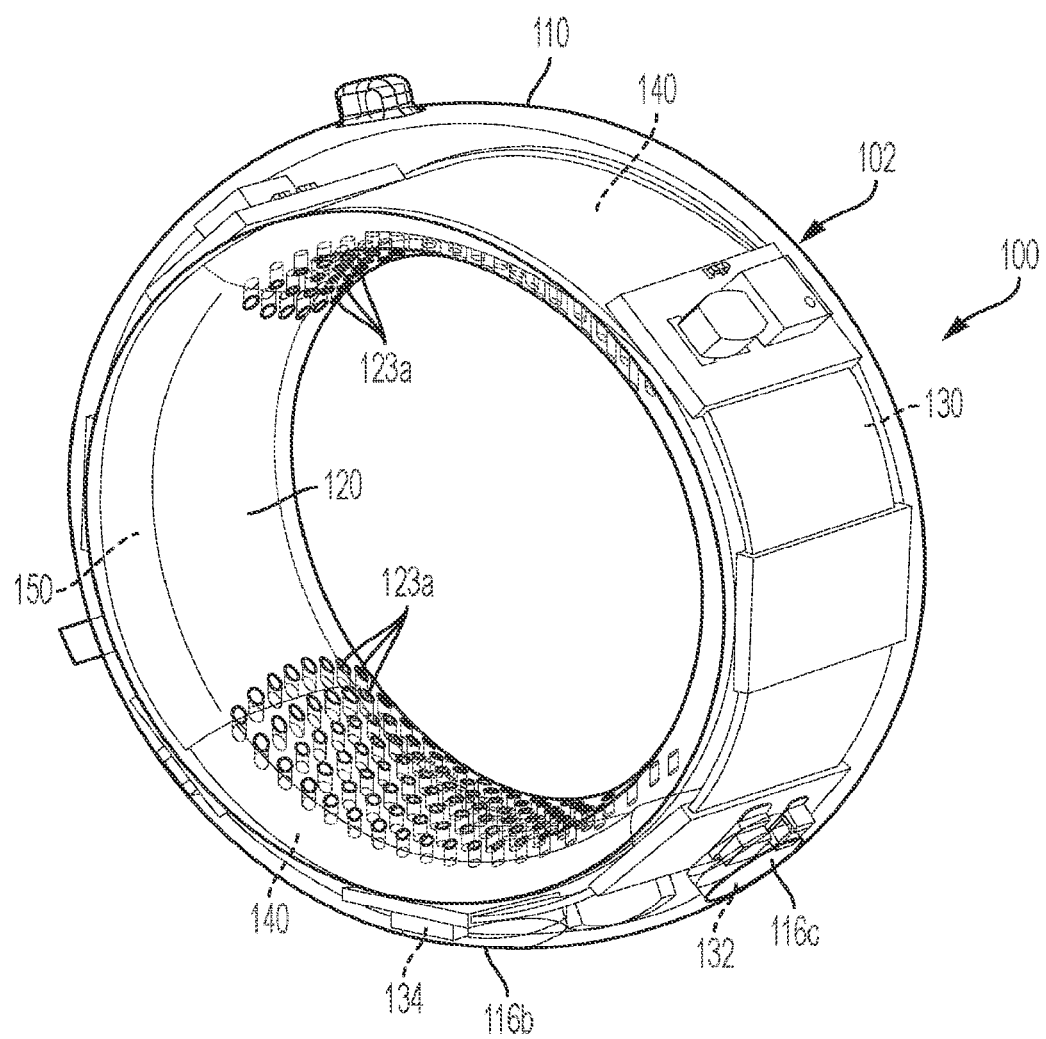
FIG. 7 illustrates the flex circuit of FIG. 6A positioned within the housing of FIG. 5A. The outer and inner covers are transparent for ease of viewing the flex circuit and the various electronic components located within the housing.

Referring to FIGS. 6A-6D and 7, various electronic components are located within the annular interior volume 102v of the housing 102 and are supported by one or more flex circuits 130 that can be shaped to conform with the curvature of the annular interior volume 102v of the housing 102. Flex circuits 130 may be flexible plastic substrates, such as polyimide, PEEK or transparent conductive polyester film, for example. The flex circuit(s) 130 supports optical emitters 132 and optical detectors 134, among other components. The optical emitters 132 are configured to emit light through respective windows 116a, 116c (FIGS. 8A-8B) into the ear of a subject wearing the device 100. Light scattered by the ear passes through window 116b into the photo detectors 134 (FIGS. 8A-8B). The optical emitters 132 may be one or more light-emitting diodes (LED), laser diodes (LD), compact incandescent bulbs, micro-plasma emitters, IR blackbody sources, organic LEDs (OLEDs), or the like. These optical emitters may generate light at one primary wavelength or they may be multi-wavelength emitters, capable of generating a plurality of distinct optical wavelengths or a broad range of optical wavelengths. The optical detectors 134 may be one or more photodiodes, photodetectors, phototransistors, thyristors, solid state devices, optical chipsets, detector arrays, digital cameras (such as CCD cameras, CMOS cameras, or the like), digital imagers, or the like. The optics of the optical emitters and optical detectors may be translucent or diffuse. Translucent optics may be useful for picking up weak optical signals, and diffuse optics may be useful for ameliorating motion artifacts. Methods of generating diffuse optics (to creating scattering at the surface) are well-known in the art.

The optical emitters 132 and optical detectors 134 serve the function of one or more biometric sensors, such as a photoplethysmography (PPG) sensor, etc. Other physiological (biometric) sensors may be included as well, such as sensors for measuring physiological properties such as vital signs (heart rate, ECG, EEG, EMG, respiration rate, blood pressure, SpO2, core body temperature, brain activity, and the like) or other biometrics. Additionally, a processor 170 may be used to process PPG signals and inertial signals (i.e., as from an inertial sensor) into various biometrics (heart rate, breathing rate, blood pressure, cardiac status, SpO2, blood pulse volume, blood hydration, and the like) or various activity parameters (such as distance traveled, steps traveled, cadence, pace, speed, activity status/characterization, and the like).

Embodiments of the present invention are not limited to the illustrated configuration or location of the optical emitters 132 and the optical detectors 134. Various numbers, configurations and locations of optical emitters 132 and optical detectors 134 may be utilized in accordance with embodiments of the present invention. For example, FIG. 6E illustrates a configuration of multiple pairs of optical emitters 132 and detectors 134 in adjacent relationship and supported by a flex circuit 130 (illustrated in a flat configuration in the schematic illustration of FIG. 6E) according to an embodiment of the present invention. The optical emitters 132 illustrated in FIG. 6E are configured to emit light radially from the edge 102e of the housing 102 (i.e., through the annular wall 112 of the outer cover 110) into the ear of a wearer, and the optical detectors 134 are configured to collect light entering the edge 102e of the housing 102 radially from the ear of the wearer (i.e., through the annular wall 112 of the outer cover 110).

In FIG. 6E, each pair of optical emitters 132 is separated from an adjacent pair of optical detectors 134 by an optical crosstalk barrier 135. These optical crosstalk barriers 135 are configured to prevent light from the optical emitters 132 directly reaching the optical detectors 134 (i.e., crosstalk). The optical crosstalk barriers 135 may be formed from material that is opaque (at least to the optical emission wavelength(s) of the optical emitters 132) and/or that is reflective in nature. The flex circuit 130 may be rolled-up or otherwise bent/shaped to conform to the annular structure of the housing 102.

In addition, adjacent groups of optical emitters 132 and optical detectors 134 can be isolated from the other groups of optical emitters 132 and optical detectors 134 by optical isolation barriers 137, as illustrated in FIG. 6E. These optical isolation barriers 137 are configured such that light emitted by a respective pair of optical emitters 132 can only be detected by the nearby optical detectors 134 (i.e., the detectors 134 that are within the same optical isolation barriers 137 as the optical emitters 132). These optical isolation barriers 137 may be formed from material that is opaque (at least to the optical emission wavelength(s) of the optical emitters 132) and/or that is reflective in nature.

In some embodiments, the optical crosstalk barriers 135 and optical isolation barriers 137 may comprise the same structure and be configured to surround the optical emitters 132 and optical detectors 134 respectively and serve as optical cladding for light-guiding purposes. In such case, it may be beneficial to have smooth, as opposed to sharp, edges in the cladding to prevent unwanted optical scatter. A specular surface along the walls of the cladding may support light-guiding. Alternatively, a roughened surface may support collimation of the light by absorbing off-angle photons. For example, it may be desirable to have the light beams leave the optical emitters 132 in a collimated fashion, such that the light beam direction is largely perpendicular to the surface of the optical emitters 132. Similarly, it may be desirable to have the light beams enter an optical detector 134 in a collimated fashion such that the light beam direction is largely perpendicular to the surface of the optical detector 134.

Figure 6E:
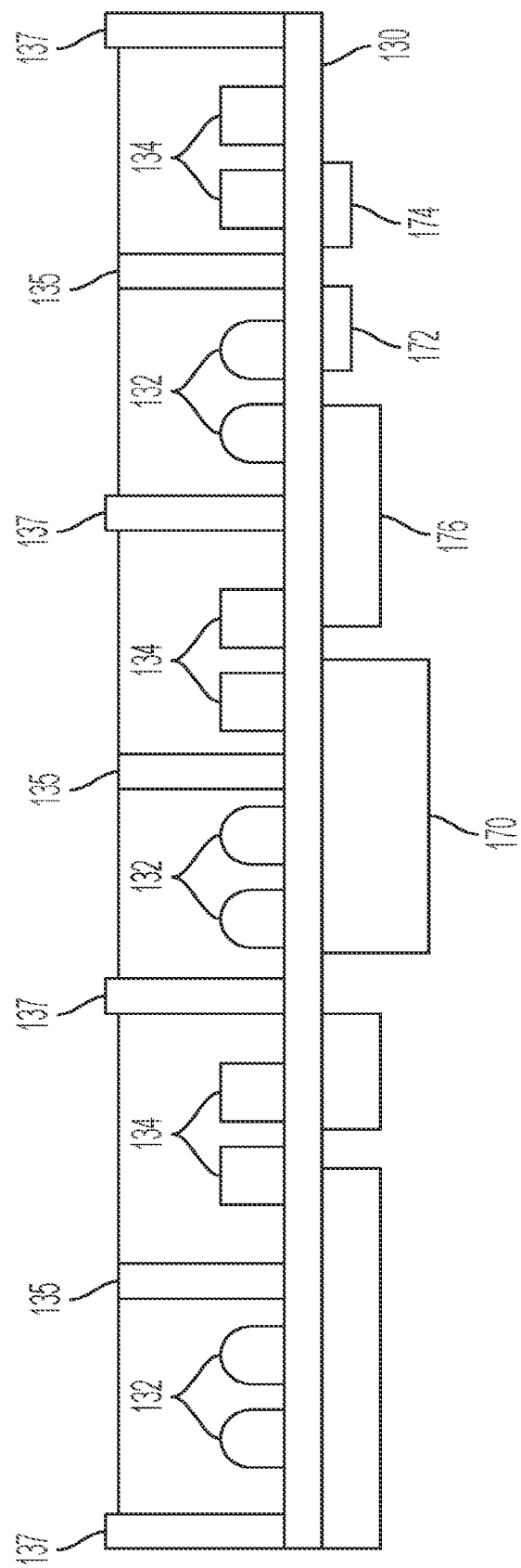
FIG. 6E is a schematic illustration of an arrangement of optical emitters and detectors and other electronic components on a flex circuit, as well as optical isolation barriers and optical crosstalk barriers, according to some embodiments of the present invention.
Figure 6F:
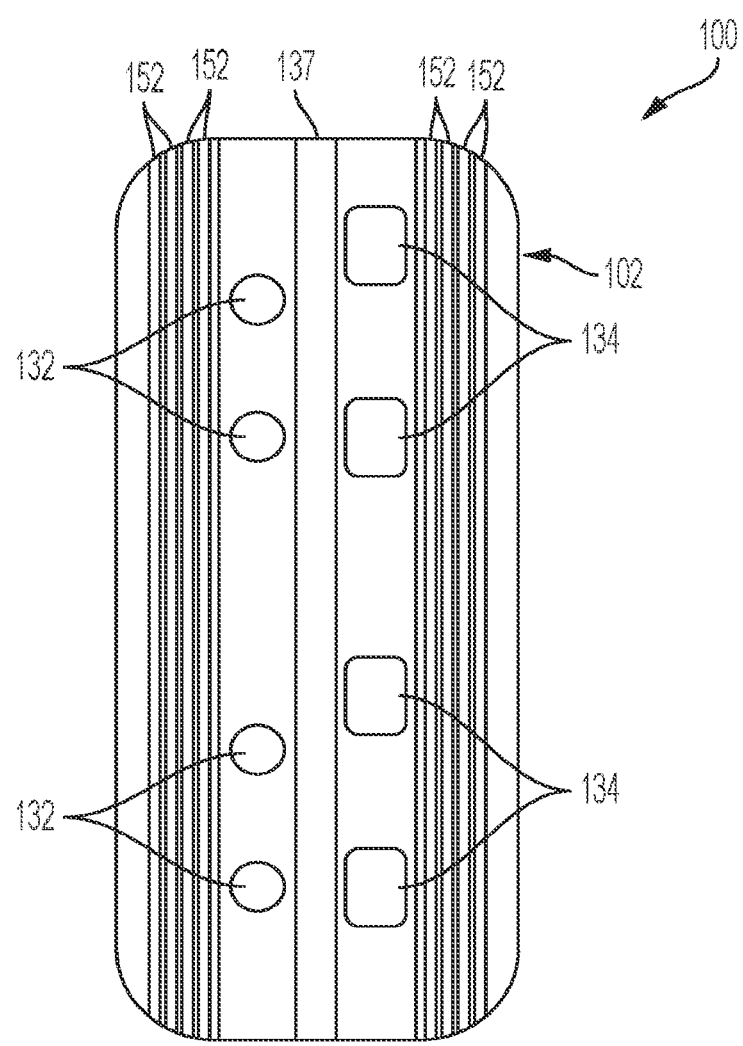
FIG. 6F is a schematic illustration of a side view of a wearable device according to some embodiments of the present invention that illustrates exemplary locations for inductive charging coils.

An alternate configuration for optical emitters and detectors is presented in FIG. 6F. In FIG. 6F, the optical emitters 132 and optical detectors 134 are radially distributed across the ring-shaped housing 102, as shown in FIG. 6E, but a major difference is that the array of emitters 132 and the array of detectors 134 are separated from each other by an optical isolation barrier 137, such that the array of optical emitters 132 and the array of optical detectors 134 are largely optically isolated from each other. The array of emitters 132 and the array of detectors 134 may each be covered by a layer of optically transparent material (such as silicone, epoxy, polycarbonate, or the like) separated by the optical isolation barrier 137. This optically transparent material may help protect the emitting/detecting structures while still enabling light transmission. A key benefit of the configuration of FIG. 6F may be that the emitter side and detector side of the optical isolation barrier 137 can each serve as a distributed radial light guide, which can help distribute light more evenly across each side of the loop or ring-shaped housing 102 and, hence, better couple light between the body of the wearer of the device 100 and the optical emitters 132 and optical detectors 134. Additionally, the overall intensity of distributed light beams (such as radial beams) can be less sensitive to motion artifacts than isolated light beams (such as point sources or more localized light beams). This can help with creating stabilized light beams with a higher percentage of pulsating blood information and a lower percentage of unwanted motion artifacts.

Figure 5B:
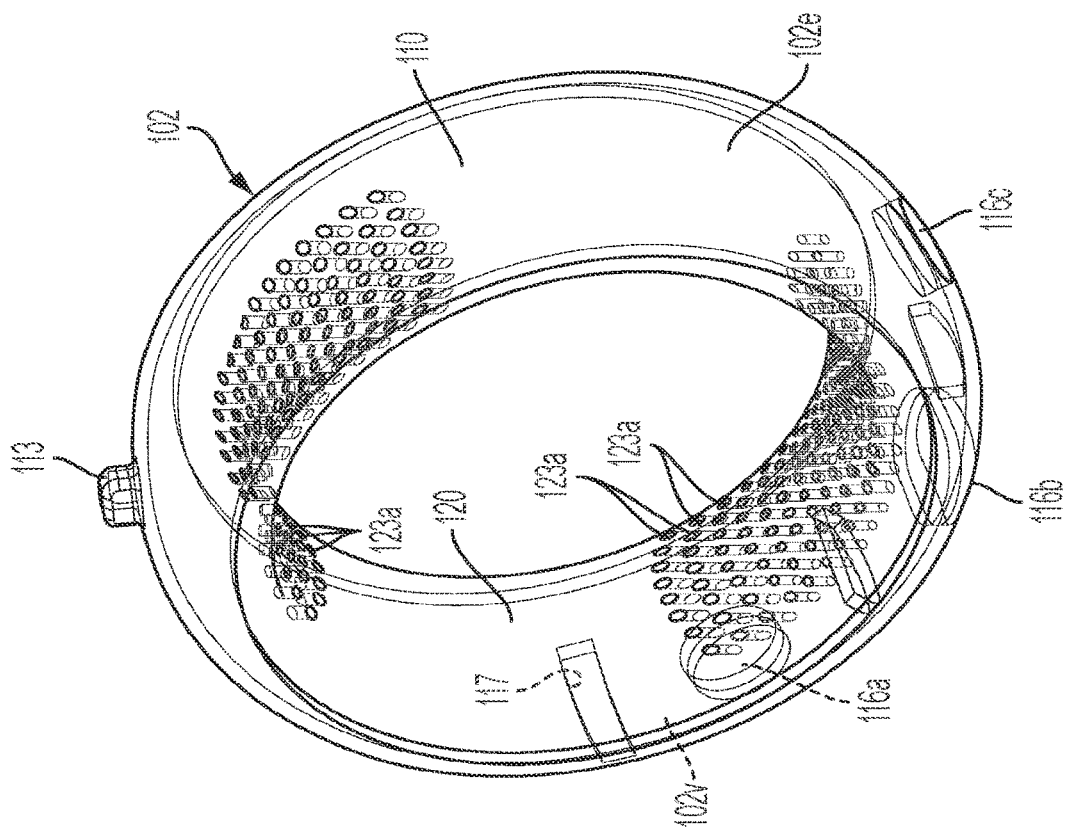
FIG. 5B illustrates the wearable device of FIGS. 2A and 2B with protruding light guides.
Figure 6G:
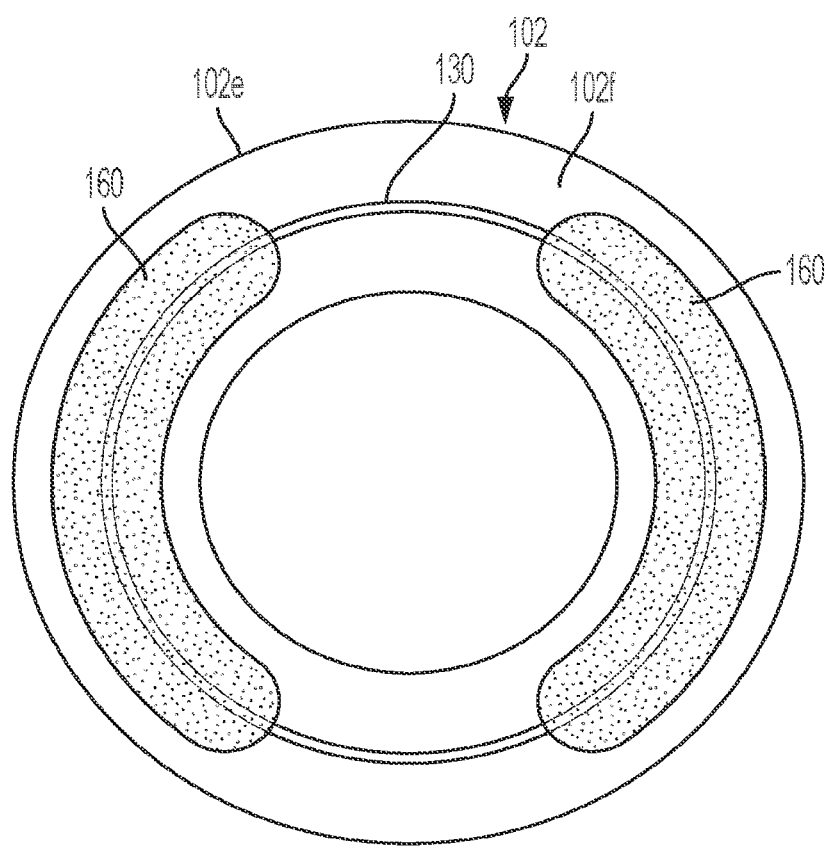
FIG. 6G is a schematic illustration of light guiding material that may be utilized within wearable devices according to some embodiments of the present invention.
Figure 6H:
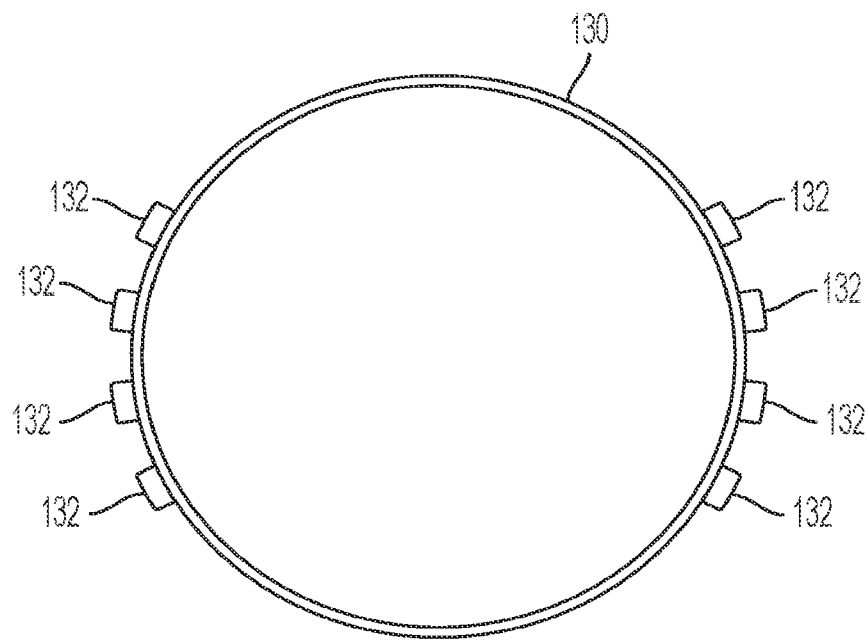
FIG. 6H illustrates a flex circuit with a plurality of edge-emitting LEDs, according to some embodiments of the present invention.

In other embodiments, at least some of the optical emitters 132 may be edge-emitters (FIG. 6H), such as edge-emitting LEDs or the like, and the optical crosstalk barriers 135 and/or optical isolation barriers 137 may be configured to direct light out of the side or face 102f of the housing 102 through one or more windows (not shown) and via light-guiding material 160, as shown in FIG. 6G. The benefit of this configuration is that the concha region of the ear and other parts of the ear may be interrogated by light directly. Also, with at least one detector 134 positioned to measure light through at least one window 116b (FIGS. 5A, 5B), the optical emitter path through the side or face 102f of the housing 102 and the optical detector path through the edge 102e of the housing 102 are approximately orthogonal to each other. This may create a longer optical path through the pulsating tissue (for example, such as an optical path through the conchae and through the anti-tragus) of the subject and hence create a higher pulsating optical signal-to-noise than a configuration where the one or more emitters and one or more detectors are exposed to roughly the same plane of tissue.

In some embodiments, the optical crosstalk barriers 135 and optical isolation barriers 137 can be formed as part of one or both of the outer and inner covers 110, 120. For example, FIG. 4B illustrates an optical crosstalk barrier 135 extending from the inner surface 112b of the outer cover 110 between windows 116a and 116b In some embodiments, light guiding material may be provided within the housing 102. The light guiding material may be used to guide light from one or more optical emitters 132 to one or more windows 116a, 116c in the edge 102e of the housing 102. In addition, or alternatively, light guiding material may be used to guide light collected through the window 116b to the optical detectors 134. In such case, the light guiding may be configured to direct light from the ear into window 116b at the outer edge 102e of the housing 102 to reach the detector(s) 134. Such light guiding material may facilitate placement of the optical emitters 132 and/or optical detectors 134 within the housing 102 in a non-line of sight manner with the respective windows 116a, 116b, 116c.

In addition, in some embodiments, light guides 118 may protrude from one or more of the respective windows 116a, 116b, 116c, as illustrated in FIG. 5B. The light guides 118 extending from windows 116a and 116c facilitate directing light from the optical emitters 132 into the skin of the ear of the wearer, and the light guide 118 extending from window 116b facilitates collecting light from the skin of the ear and directing the collected light to the optical detectors 134. The light guides 118 may facilitate collimating the light as well as helping anchor the optics at the same location of the skin. The light guides 118 can have various configurations. Light guides and light guiding material that may be used in accordance with the various embodiments of the present invention are described in U.S. Pat. No. 8,788,002, which is incorporated herein by reference in its entirety.

In some embodiments, an optical filter may be integrated within the light guiding material 160. For example, the light guiding material 160 may include a material having an optically filtering dye or a material which inherently filters one or more wavelengths of light. As one example, the light guiding material 160 may include, wholly or partially, a dye therewithin. As one specific example, a dye, such as an infrared dye designed to block visible wavelengths but pass IR wavelengths may be utilized. For example, polycarbonate or acrylic light guiding material 160 dyed with Filtron® absorptive dye E800 (Gentex Corporation, Carbondale, PA), would facilitate both light-guiding and IR-pass filtering functionality. Alternatively, another example of such an integrated physical optical filter comprises absorptive dyes available from Sabic (Riyadh, Saudi Arabia) dispersed in polycarbonate and/or acrylic to create an edge or long-pass optical filter. The light guiding material 160 may be partially or wholly comprised of such a material, thereby facilitating the combinational purpose of light guiding and optical filtering. A few additional non-limiting examples of an inherently filtering material includes sapphire, which absorbs some infrared (IR) wavelengths, glass, which absorbs some ultraviolet (UV) wavelengths, and dyed glass (for which dye combinations can be applied to enable optical filtering that is low-pass, high-pass, band-pass, notching, and the like). However, various types of filtering material may be utilized, without limitation.

In some embodiments, an optical filter may be integrated with the optical emitters 132 and/or the optical detectors 134. For example, a bandpass filter, such as an interference filter or the like, may be disposed on an optical emitter 132 and/or optical detector 134. Alternatively (or additionally), an optical filter effect may be integrated within the semiconductor material comprising the optical emitter 132 and/or optical detector 134, such as by depositing alternating optically-transparent layers (such as oxides and/or nitrides), selective ion implantation of certain regions within silicon, or by band-gap engineering within compound semiconductors, such as the AlInGaAs or AlInGaN system of semiconductor engineering.

In some embodiments of the present invention, the light-guiding material 160 may include polarizing material. Exemplary polarizing material that can be used in accordance with embodiments of the present invention is available from American Polarizers, Inc., Reading, Pennsylvania, as well as Edmund Optics, Barrington, New Jersey. A key benefit of a cross-polarizing implementation, where the optical emitter polarizer is configured to be orthogonally polarized with respect to the optical detector polarizer, may be that unwanted specular reflection is attenuated such that the light beam collected by the optical detector comprises a higher percentage of photons that have passed through a blood flow region of the body.

Figure 11:
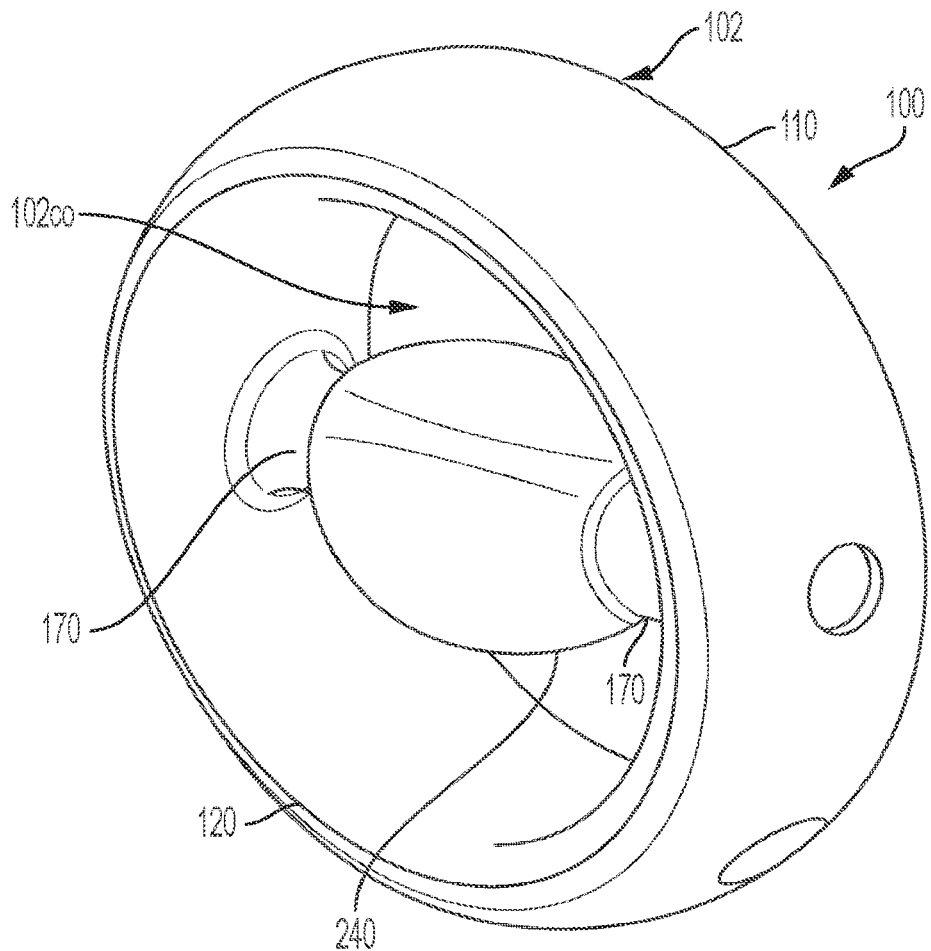
FIG. 11 is a perspective view of a ring-shaped wearable device according to another embodiment of the present invention, wherein a speaker is located external to the housing and positioned within the central opening of the housing via at least one support member.

Referring back to FIG. 6A, a pair of speakers 140 are secured to the flex circuit 130 and are positioned in opposing relationship with each other, as illustrated. As shown in FIG. 7, each speaker 140 is positioned within the housing 102 so as to align with a respective one of the sets of apertures 123a so that sound from the speakers 140 can pass therethrough. In the illustrated embodiment, the speakers 140 have an arcuate configuration such that they can conform with the curvature of the annular interior volume 102v of the housing 102. However, speakers 140 can have various shapes and configurations. Alternatively, according to other embodiments of the present invention and as illustrated in FIG. 11, a speaker 240 may be positioned within the central opening 102co of the housing 102 and may be supported by one or more support members 170 that extend radially inwardly from the inner housing 120. At least some of the apertures 123a (FIG. 7) may also serve as apertures for a microphone within the housing 102 (i.e., allow sound to pass through the housing 102 into a microphone within the housing 102). In addition to microphones for receiving voice communications by a wearer of the device 100, bone conducting speaker/microphones may also be utilized.

A power source 150 is supported by the flex circuit 130, as illustrated in FIG. 6A, and supplies power to the various electronic components of the device 100. The power source 150 may be a battery (such as a lithium polymer battery or other portable battery) or other power source sufficiently small to fit within the housing 102 (such as an energy harvesting source). The power source 150 may be charged via a charge port, such as a USB charge port, for example. In the illustrated embodiment, the battery is a rechargeable battery, and a charging coil 152 is provided to transfer electrical charge to the rechargeable battery when the housing 102 is within a pre-determined range of an inductive charging coil. In some embodiments, the charging coil 152 may be supported by the flex circuit 130. In other embodiments, the charging coil 152 may be supported within the housing separate from the flex circuit 130. In other embodiments, the charging coil 152 may be provided external to the housing 102 or as part of the housing 102, i.e., embedded within the material of the outer or inner covers 110, 120. In some embodiments, a plurality of charging coils may be provided, as illustrated in FIG. 6F.

In some embodiments, charging coils 152 utilized with embodiments of the present invention are made up of cable strands, for example with about eighteen (18) turns of 0.28 mm wire. This provides a coil with a conductor bundled diameter of about 1.25 mm that would circle the perimeter of the device as shown in FIG. 6F.

Batteries utilized in accordance with embodiments of the present invention can have various sizes. For example, a battery 150 with a volume of about 1700 mm3 can provide about 80 mA-h, and a battery with a volume of about 420 mm3 can provide about 20 mA-h.

The flex circuit 130 may support various other electronic components. For example, a processor, a wireless module for communicating with a remote device, a microphone, an auscultatory sensor, an environmental sensor, a motion sensor, a memory storage device, etc., may be supported by one or more flex circuits 130. Non-limiting examples of environmental sensors may include an ambient light sensor, humidity sensor, ambient temperature sensor, or the like. Non-limiting examples of motion sensors include inertial sensors (e.g., accelerometers, gyroscopes, etc.), mechanical motion sensors, bone conduction sensors, Hall-effect sensors, optical sensors, acoustic sensors, or the like.

In some embodiments, it may be important to locate inertial sensor(s) away from the mechanical audio components (i.e., the microphone or speaker) of a device 100, or to mechanically decouple the inertial sensor(s) from the mechanical audio components to prevent aliasing of acousto-mechanical energy into the inertial sensor(s). However, in other embodiments, it may be useful to mechanically couple at least one inertial sensor to the audio components to monitor the movement of these components and to enable feedback for controlling audio parameters via a microprocessor. Mechanical coupling can be achieved by locating an inertial sensor near a mechanical audio component and/or to have the inertial sensor and mechanical audio component connected through a rigid support structure. Alternatively, mechanical decoupling can be achieved by the reverse (e.g., locating an inertial sensor away from the mechanical audio component and/or having the inertial sensor and mechanical audio component connected through a flexible or mechanically damping support structure.

In some embodiments, some or all of the electronic components within the device may be encapsulated within a hydrophobic encapsulant material.

FIG. 6E schematically illustrates various additional electronic components attached to the flex circuit 130. A processor 170 may be in communication with the various components within the device 100 and may be configured to control operation thereof. For example, the processor 170 may be configured to control the optical emitters 132 to emit light, and to process signals produced by the optical detectors 134. In addition, the processor 170 may be configured to control other sensors, such as an environmental sensor 172 and a motion sensor 174, and to process signals that are produced by these other sensors. In addition, the processor 170 may be configured to control wireless communications via a wireless communication module 176. The processor 170 may also filter noise from the sensor signals, actively remove motion noise, actively remove environmental noise, and the like.

Figure 12:
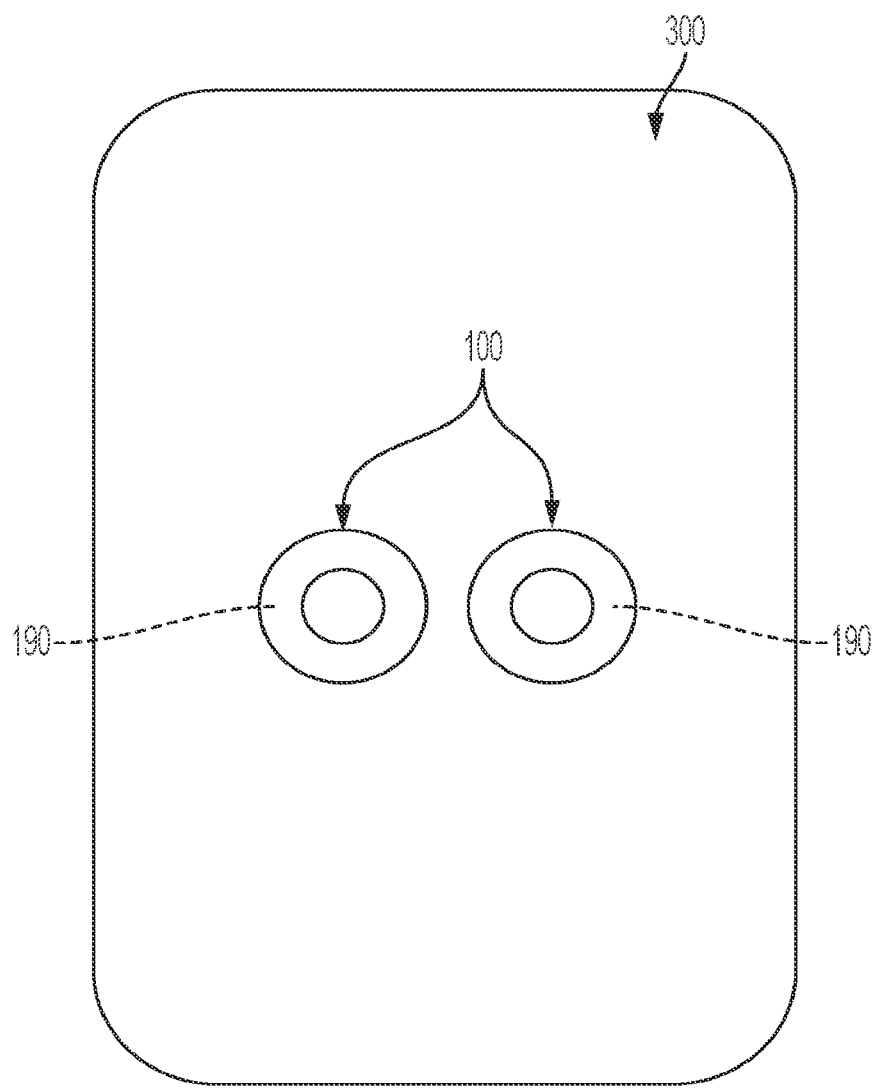
FIG. 12 is a schematic illustration of a pair of ring-shaped wearable devices according to embodiments of the present invention and that are configured to be magnetically secured to the back of a mobile device, such as a smartphone.

Referring to FIG. 12, wearable devices 100 according to some embodiments of the present invention may include one or more magnets 190 that are configured to magnetically secure the devices 100 to another device, such as a mobile phone 300, in order to provide convenient storage and access. Such magnets 190 may be within the housing 102, a part of one or both of the outer and inner housings 110, 120, or located external to the housing 102.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

What is claimed is:

1. A wearable device, comprising:
   a ring-shaped housing having a central opening and defining an annular interior volume and an outer annular surface, wherein the housing is configured to be worn within an ear of a subject such that an ear canal of the ear is exposed by the central opening;
   at least one optical emitter within the housing;
   at least one optical detector within the housing, wherein the housing comprises at least one window through which light can be delivered from the at least one optical emitter to the ear, and through which light from the ear can be delivered to the at least one optical detector; and a stabilizer member protruding from the outer annular surface and configured to engage a portion of the ear of the subject.

2. The wearable device of claim 1, wherein the at least one window is at least one transparent portion in the housing or at least one opening in the housing.

3. The wearable device of claim 1, further comprising a covering of conformable, resilient material removably secured to the housing.

4. The wearable device of claim 1, wherein the at least one window comprises first and second windows, wherein the first window is configured to deliver light from the at least one optical emitter to the ear, and wherein the second window is configured to deliver light from the ear to the at least one optical detector.

5. The wearable device of claim 1, further comprising at least one speaker within the housing, and wherein the housing further comprises one or more apertures through which sound from the at least one speaker can pass.

6. The wearable device of claim 5, wherein the at least one speaker has an arcuate configuration.

7. The wearable device of claim 1, further comprising a speaker positioned within the central opening via at least one support member extending radially inwardly from the housing.

8. The wearable device of claim 1, wherein the housing comprises a conformable, resilient material.

9. The wearable device of claim 1, wherein the at least one optical emitter and the at least one optical detector comprise a first optical emitter, a first optical detector, a second optical emitter, and a second optical detector, wherein the first optical detector and first optical emitter are in adjacent relationship at a first location within the housing with a first optical crosstalk barrier therebetween, and wherein the second optical detector and second optical emitter are in adjacent relationship at a second location within the housing with a second optical crosstalk barrier therebetween.

10. The wearable device of claim 9, wherein the first optical detector and first optical emitter are optically isolated from the second optical detector and second optical emitter via at least one optical barrier.

11. The wearable device of claim 1, further comprising a flex circuit that supports the at least one optical emitter and the at least one optical detector within the housing.

12. The wearable device of claim 1, further comprising:
at least one processor within the housing that is operably coupled to the at least one optical emitter and to the at least one optical detector, wherein the at least one processor is configured to control the at least one optical emitter to emit light, and wherein the at least one processor is configured to process signals produced by the at least one optical detector; and
a power source within the housing that is electrically connected to the at least one processor, the at least one optical detector, and the at least one optical emitter.

13. The wearable device of claim 12, wherein the power source comprises at least one rechargeable battery, and wherein the housing further comprises at least one charging coil configured to transfer electrical charge to the at least one rechargeable battery when the housing is within a predetermined range of an inductive charging coil.

14. The wearable device of claim 1, further comprising a wireless communication unit within the housing that is configured to wirelessly communicate with a remote device.

15. The wearable device of claim 14, wherein the at least one processor is operably coupled to the wireless communication unit.

16. The wearable device of claim 1, further comprising at least one motion sensor within the housing that is configured to sense body motion of the subject wearing the device.

17. The wearable device of claim 1, further comprising light guiding material within the housing that is in optical communication with the at least one optical emitter and the at least one window and that is configured to deliver light from the at least one optical emitter to the at least one window.

18. The wearable device of claim 1, further comprising light guiding material within the housing that is in optical communication with the at least one optical detector and the at least one window and that is configured to deliver light from the at least one window to the at least one optical detector.

19. The wearable device of claim 1, further comprising at least one magnet configured to magnetically secure the wearable device to another device.

* * * * *